United States Patent
Goldman et al.

(10) Patent No.: US 8,263,406 B2
(45) Date of Patent: *Sep. 11, 2012

(54) ENRICHED OR PURIFIED POPULATION OF MOTOR NEURONS AND ITS PREPARATION FROM A POPULATION OF EMBRYONIC STEM CELLS

(75) Inventors: Steven A. Goldman, Webster, NY (US); Neeta Singh Roy, New York, NY (US); Takahiro Nakano, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/865,637

(22) Filed: Jun. 10, 2004

(65) Prior Publication Data

US 2005/0003544 A1 Jan. 6, 2005

Related U.S. Application Data

(60) Provisional application No. 60/477,566, filed on Jun. 11, 2003.

(51) Int. Cl.
*C12N 15/87* (2006.01)
*C12N 15/88* (2006.01)
*C12N 15/89* (2006.01)
*C12N 5/071* (2010.01)

(52) U.S. Cl. ........ 435/455; 435/368; 435/458; 435/459

(58) Field of Classification Search .............. 435/325, 435/377, 455, 435, 458, 368, 459; 424/93.21
See application file for complete search history.

(56) References Cited

U.S. PATENT DOCUMENTS

| | | | |
|---|---|---|---|
| 5,491,084 A | 2/1996 | Chalfie et al. | |
| 5,928,947 A * | 7/1999 | Anderson et al. | 435/455 |
| 6,245,564 B1 | 6/2001 | Goldman et al. | |
| 6,692,957 B2 | 2/2004 | Goldman et al. | |
| 2002/0168338 A1 | 11/2002 | Baird | |
| 2004/0014210 A1* | 1/2004 | Jessell et al. | 435/368 |
| 2005/0129672 A1 | 6/2005 | Goldman et al. | |

FOREIGN PATENT DOCUMENTS
WO WO03075647 A2 9/2003

OTHER PUBLICATIONS

Yoshida et al (Cell Transplantation, 1999, 8: 427-430).*
Sumitran et al (Cell Transplantation, 1999, 8: 601-610).*
Barker et al (The Journal of Neuroscience, 2000, 20(9): 3415-3424).*
Armstrong et al (Neuroscience, 2001, 106(1): 201-216).*
Larsson et al (Brain Research Bulletin, 1999, 49(5): 367-376.*
Larsson et al (Experimental Neurology, 2001, 172: 100-114).*
Loseva et al (Brain Research, 2001, 915: 125-132).*
Larsson et al (Scand. J. Immunol. 2000, 52: 249-256).*
Bjorklund et al. Nature Neuroscience, 2000, 3(6): 537-544).*
Cao et al. Gene Therapy, 2001, 8: 1357-1362.*
Schuldiner et al. Brain Research, 2001, 913: 201-205.*
Roy et al. Nature Medicine, 2000, 6(3): 271-277.*
Wichterle et al. Cell, 2002, 110: 385-397.*
Roy et al. Experimental Neurology, 2005, 196: 224-234.*
Romano, Drug News Perspect, 16(5): 267-276, 2003.*
Du and Zhang Stem Cells Dev. 2004; 13(4):372-81.*
Li et al Nat Biotechnol. Feb. 2005;23(2):215-21.*
Keyoung et al Nat Biotechnology, Sep. 2001;19(9):843-50.*
Silani et al Neuroreport, 1998, 9, 1143-1147.*
Kato et al The Journal of Neuroscience, 1985, 5, 10, 2750-2761.*
Aparicio et al., "Detecting Conserved Regulatory Elements with the Model Genome of the Japanese Puffer Fish, Fugu rubripes," Proc. Natl. Acad. Sci. USA 92:1684-1688 (1995).
Aparicio et al., "Whole-Genome Shotgun Assembly and Analysis of the Genome of Fugu rubripes," Science 297:1301-1310 (2002).
Arber et al., "Requirement for the Homeobox Gene Hb9 in the Consolidation of Motor Neuron Identity," Neuron 23:659-674 (1999).
Brenner et al., "Characterization of the Pufferfish (Fugu) Genome as a Compact Model Vertebrate Genome," Nature 366:265-268 (1993).
Briscoe et al., "A Homeodomain Protein Code Specifies Progenitor Cell Identity and Neuronal Fate in the Ventral Neural Tube," Cell 101:435-445 (2000).
Briscoe & Ericson, "Specification of Neuronal Fates in the Ventral Neural Tube," Curr. Opin. Neurobiol. 11:43-49 (2001).
Briscoe et al., "Homeobox Gene Nkx2.2 and Specification of Neuronal Identity by Graded Sonic Hedgehog Signalling," Nature 398:622-627 (1999).

(Continued)

*Primary Examiner* — Anoop Singh
(74) *Attorney, Agent, or Firm* — LeClariRyan, a Professional Corporation

(57) ABSTRACT

The present invention is directed to a method of isolating an enriched or purified population of motor neurons from a population of embryonic stem cells. This method involves providing a population of embryonic stem cells and selecting a promoter or enhancer which functions only in the motor neurons selected. A nucleic acid molecule encoding a marker protein under control of the promoter or enhancer is introduced into the induced population of embryonic stem cells. The motor neurons are allowed to express the marker protein and, the cells expressed in the marker protein are separated from the population of embryonic stem cells. The population of embryonic stem cells can be induced to produce a mixed population of cells comprising motor neurons before or after a nucleic acid molecule encoding the marker protein under control of the promoter enhancer is introduced into the population of embryonic stem cells. As a result, an enriched or purified population of motor neurons is isolated.

18 Claims, 6 Drawing Sheets

OTHER PUBLICATIONS

Chan & Mann, "A Structural Model for a Homeotic Protein-Extradenticle-DNA Complex Accounts for the Choice of HOX Protein in the Heterodimer," Proc. Natl. Acad. Sci. USA 93:5223-5228 (1996).
Dasen et al., "Motor Neuron Columnar Fate Imposed by Sequential Phases of Hox-c Activity," Nature 425:926-933 (2003).
Di Rocco et al., "Functional Dissection of a Transcriptionally Active, Target-Specific Hox-Pbx Complex," EMBO J. 16:3644-3654 (1997).
Gage et al., "The Bicoid-Related Pitx Gene Family in Development," Mammal. Genome 10:197-200 (1999).
Gaunt et al., "Expression of the Mouse Goosecoid Gene During Mid-Embryogenesis May Mark Mesenchymal Cell Lineages in the Developing Head, Limbs and Body Wall," Development 117:769-778 (1993).
Goridis & Brunet, "Transcriptional Control of Neurotransmitter Phenotype," Curr. Opin. Neurobiol. 9:47-53 (1999).
Heinemeyer et al., "Databases on Transcriptional Regulation: TRANSFAC, TRRD and COMPEL," Nucleic Acids Res. 26:362-367 (1998).
Helms et al., "Autoregulation and Multiple Enhancers Control Math1 Expression in the Developing Nervous System," Development 127:1185-1196 (2000).
Ho et al., "Site-Directed Mutagenesis by Overlap Extension Using the Polymerase Chain Reaction," Gene 77:51-59 (1989).
Hogan et al., Manipulating the Mouse Embryo, Cold Spring Harbor Laboratory Press, Cold Spring Harbor (1994) (Table of Contents only).
Jessell & Melton, "Diffusible Factors in Vertebrate Embryonic Induction," Cell 68:257-270 (1992).
Jessell, T.M., "Neuronal Specification in the Spinal Cord: Inductive Signals and Transcriptional Codes," Nat. Rev. Genet. 1:20-29 (2000).
Jungbluth et al., "Specification of Distinct Motor Neuron Identities by the Singular Activities of Individual Hox Genes," Development 126:2751-2758 (1999).
Lee et al., "Analysis of Embryonic Motoneuron Gene Regulation: Derepression of General Activators Function in Concert with Enhancer Factors," Development 131:3295-3306 (2004).
Lee & Pfaff, "Synchronization of Neurogenesis and Motor Neuron Specification by Direct Coupling of bHLH and Homeodomain Transcription Factors," Neuron 38:731-745 (2003).
Levy et al., "Retroviral Transfer and Expression of Humanized, Red-Shifted Green Fluorescent Protein Gene Into Human Tumor Cells," Nature Biotechnol. 14:610-614 (1996).
Liu et al., "Assigning the Positional Identity of Spinal Motor Neurons: Rostrocaudal Patterning of Hox-c Expression by FGFs, Gdf11, and Retinoids," Neuron 32:997-1012 (2001).
Lumsden & Krumlauf, "Patterning the Vertebrate Neuraxis," Science 274:1109-1115 (1996).
Maconochie et al., "Cross-Regulation in the Mouse HoxB Complex: The Expression of Hoxb2 in Rhombomere 4 is Regulated by Hoxb1," Genes Dev. 11:1885-1895 (1997).
Muhr et al., "Groucho-Mediated Transcriptional Repression Establishes Progenitor Cell Pattern and Neuronal Fate in the Ventral Neural Tube," Cell 104:861-873 (2001).
Müller et al., "Search for Enhancers: Teleost Models in Comparative Genomic and Transgenic Analysis of cis Regulatory Elements," Bioessays 24:564-572 (2002).
Ovitt et al., Microinjection and Transgenesis, pp. 427-437 (1997).
Pierani et al., "Control of Interneuron Fate in the Developing Spinal Cord by Progenitor Homeodomain Protein Dbx1," Neuron 29:367-384 (2001).
Quandt et al., "MatInd and MatInspector: New Fast and Versatile Tools for Detection of Consensus Matches in Nucleotide Sequence Data," Nucleic Acids Res. 23:4878-4884 (1995).
Roy et al., "Telomerase Immortalization of Neuronally Restricted Progenitor Cells Derived from the Human Fetal Spinal Cord," Nat. Biotechnol. 22:297-305 (2004).
Simeone et al., "A Vertebrate Gene Related to Orthodenticle Contains Homeodomain of the Bicoid Class and Demarcates Anterior Neuroectoderm in the Gastrulating Mouse Embryo," EMBO J. 12:2735-2747 (1993).
Simmons et al., "Neurogenin2 Expression in Ventral and Dorsal Spinal Neural Tube Progenitor Cells is Regulated by Distinct Enhancers," Dev. Biol. 229:327-339 (2001).
Tanabe et al., "Specification of Motor Neuron Identity by the MNR2 Homeodomain Protein," Cell 95:67-80 (1998).
Thaler et al., "Active Suppression of Interneuron Programs Within Developing Motor Neurons Revealed by Analysis of Homeodomain Factor HB9," Neuron 23:675-687 (1999).
Tiret et al., "Increased Apoptosis of Motoneurons and Altered Somatotopic Maps in the Brachial Spinal Cord of Hoxc-8-Deficient Mice," Development 125:279-291 (1998).
Vallstedt et al., "Different Levels of Repressor Activity Assign Redundant and Specific Roles to Nkx6 Genes in Motor Neuron and Interneuron Specification," Neuron 31:743-755 (2001).
Vult Von Steyern et al., "The Homeodomain Transcription Factors Islet 1 and HB9 Are Expressed in Adult Alpha and Gamma Motoneurons Identified by Selective Retrograde Tracing," Eur. J. Neurosci. 11:2093-2102 (1999).
Sambrook et al., Molecular Cloning: A Laboratory Manual, 2nd Edition, Cold Spring Harbor Laboratory Press, Cold Spring Harbor, New York (1989) (Table of Contents only).
Yee & Rigby, "The Regulation of Myogenin Gene Expression During the Embryonic Development of the Mouse," Genes Dev. 7:1277-1289 (1993).
Boillee et al., "Gene Therapy for ALS Delivers," Trends Neurosci. 27(5):235-8 (2004).
Blits et al., "Direct Gene Therapy for Repair of the Spinal Cord," 23(3-4):508-20 (2006).
Xiang et al., "Strategies to Create a Regenerating Environment for the Injured Spinal Cord," Curr Pharm Des. 11 (10):1267-77 (2005).
Sejvar et al., "Manifestations of West Nile Neuroinvasive Disease," Rev. Med. Virol. 16:209-224 (2006).
NCBI Entrez Nucleotide Results for Accession No. 129977, Jan. 10, 2003, printed Jan. 10, 2008 pp. 1-28.
NCBI Entrez Nucleotide Results for Accession No. AC006357, Jan. 10, 2003, printed Oct. 3, 2008 pp. 1-2.
Sanger Centre Group et al., "Toward a Complete Human Genome Sequence," Genome Res. 8(11):1097-108 (1998).
NCBI Entrez Nucleotide Results for Accession No. AC128478, Sep. 22, 2002, printed Oct. 3, 2008 pp. 1-2.

* cited by examiner

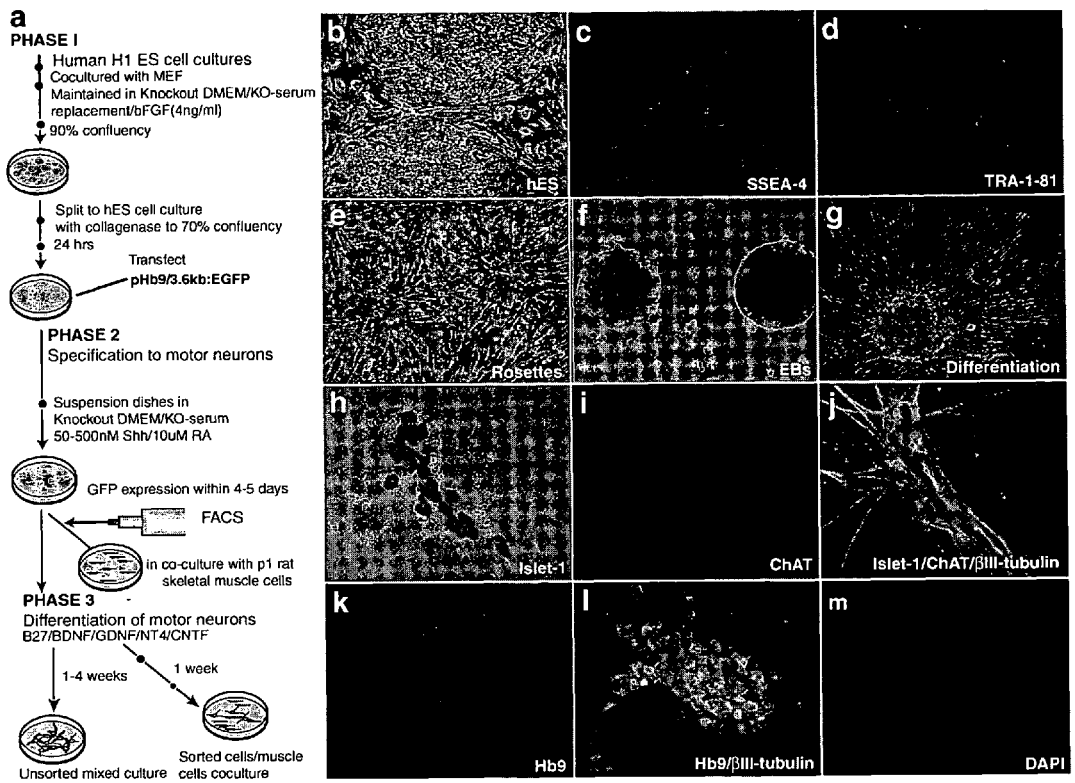
FIGURES 1A-M

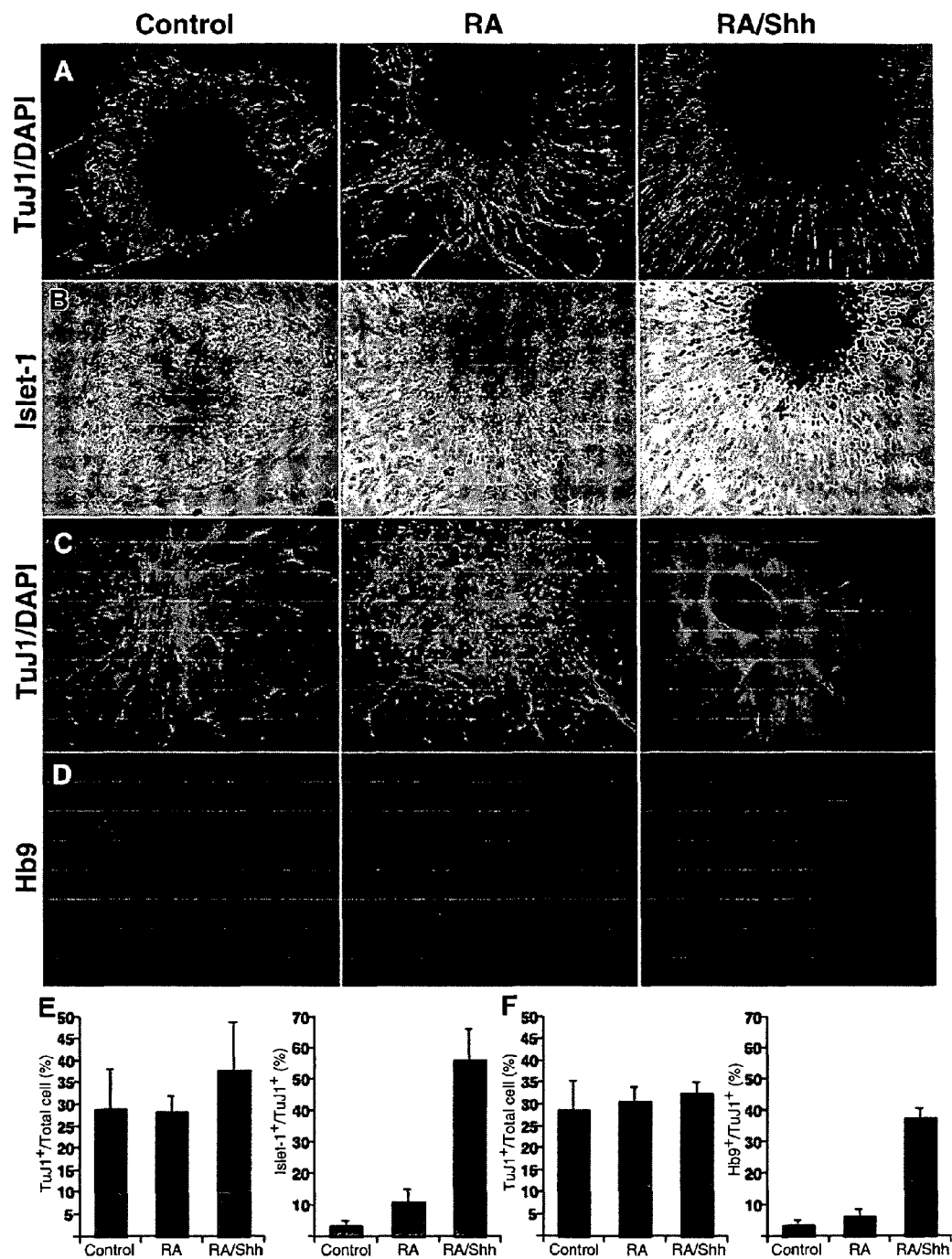
FIGURES 2A-F

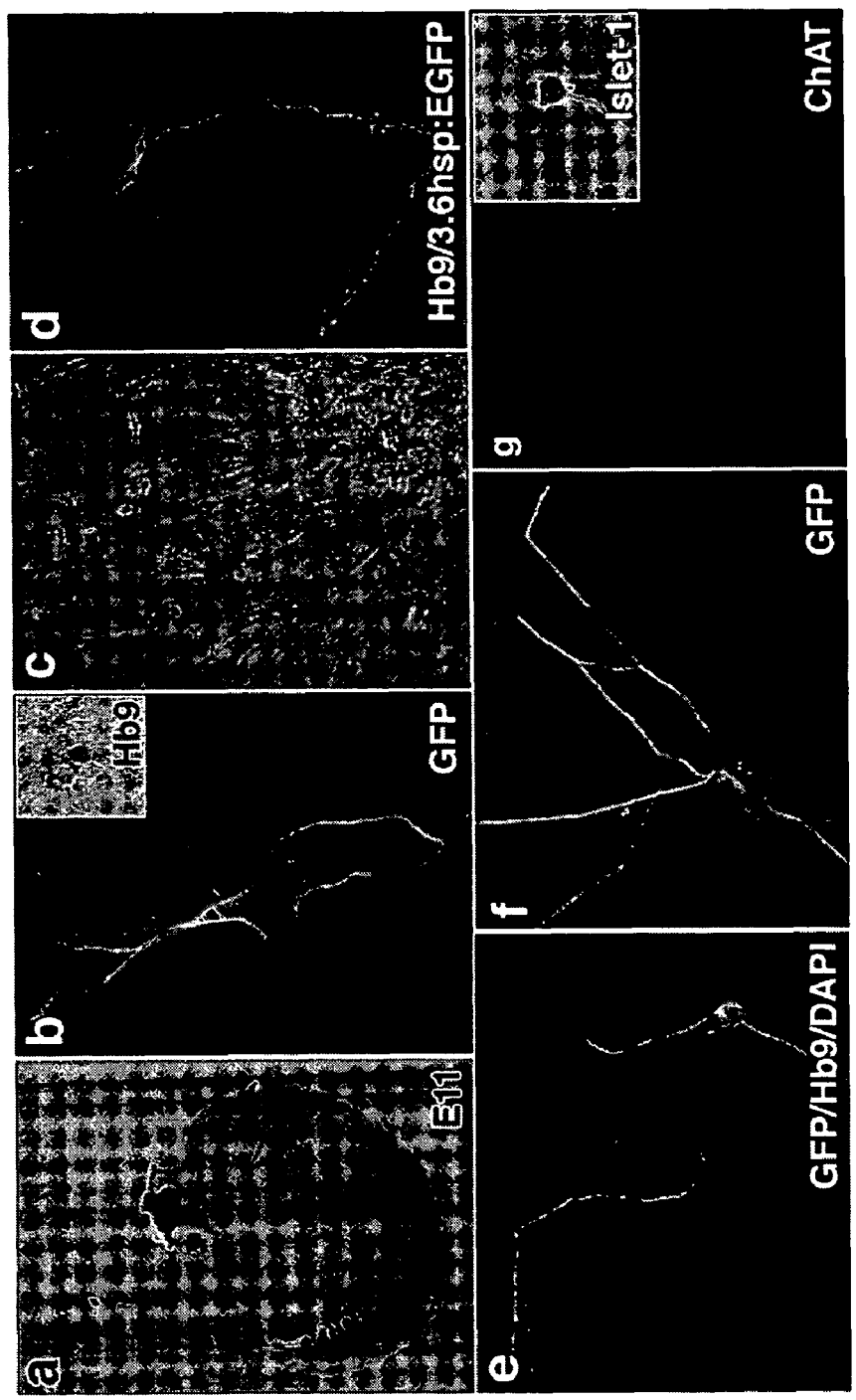
FIGURES 3A-G

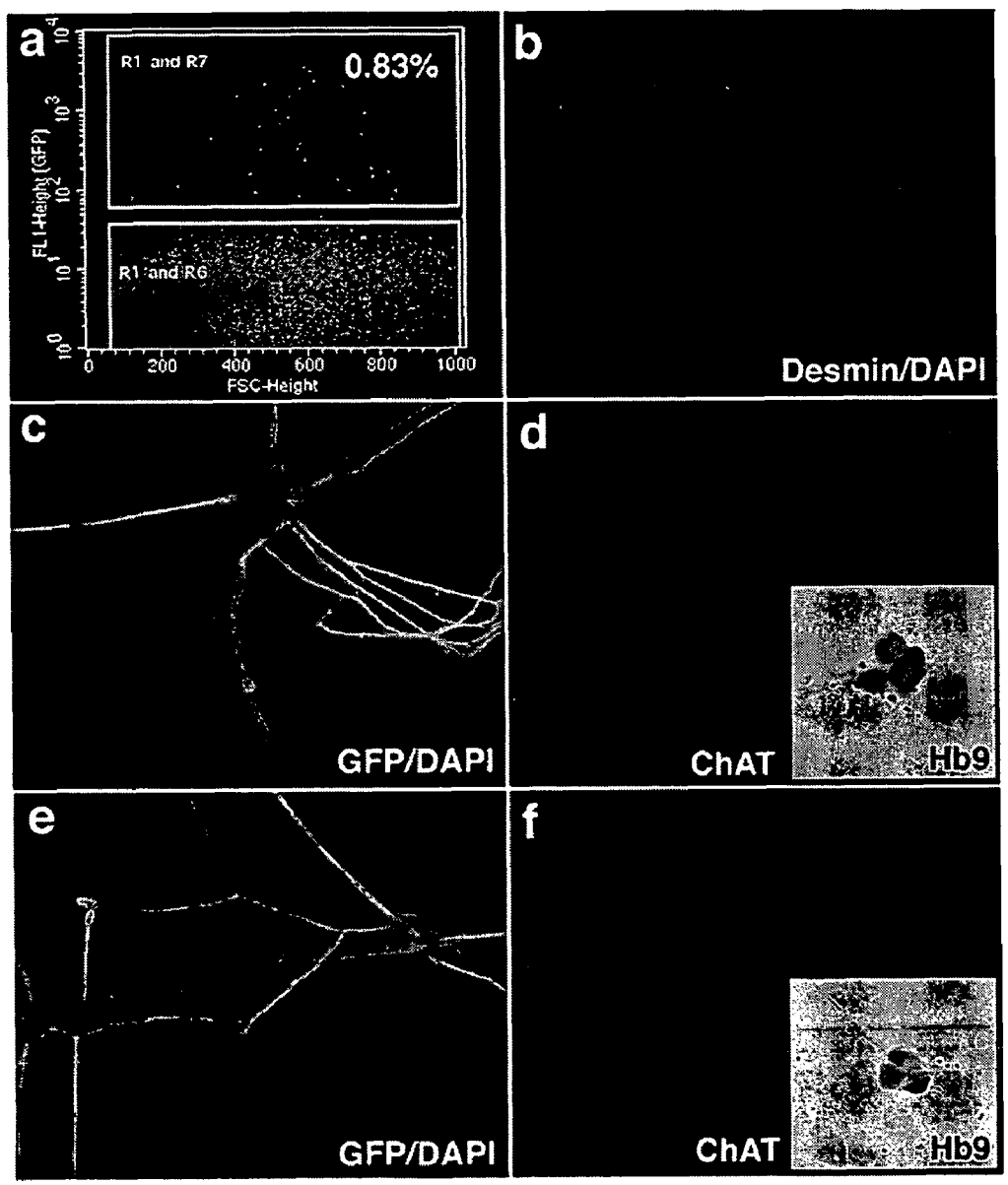
FIGURES 4A-F

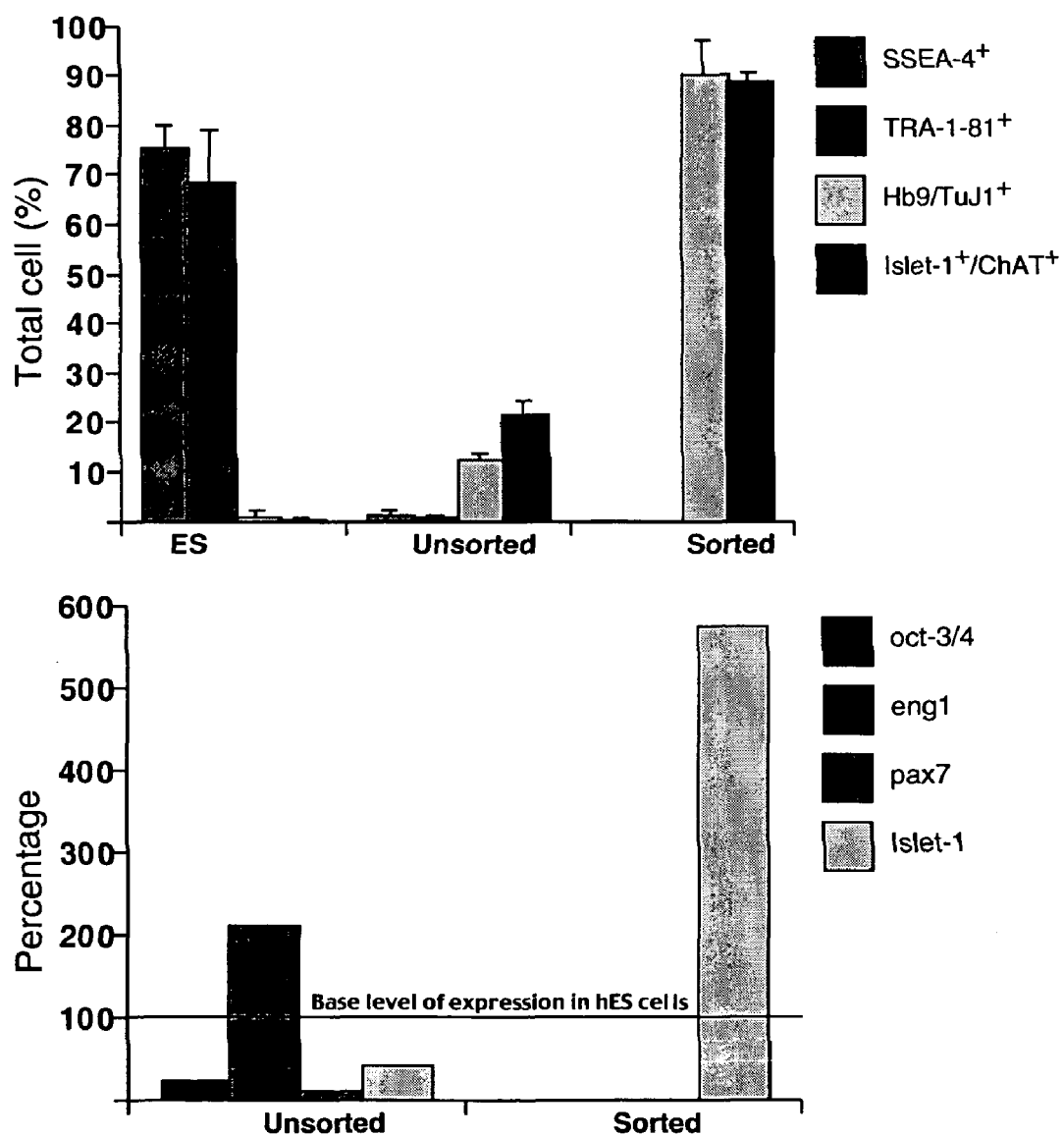
FIGURES 5A-B

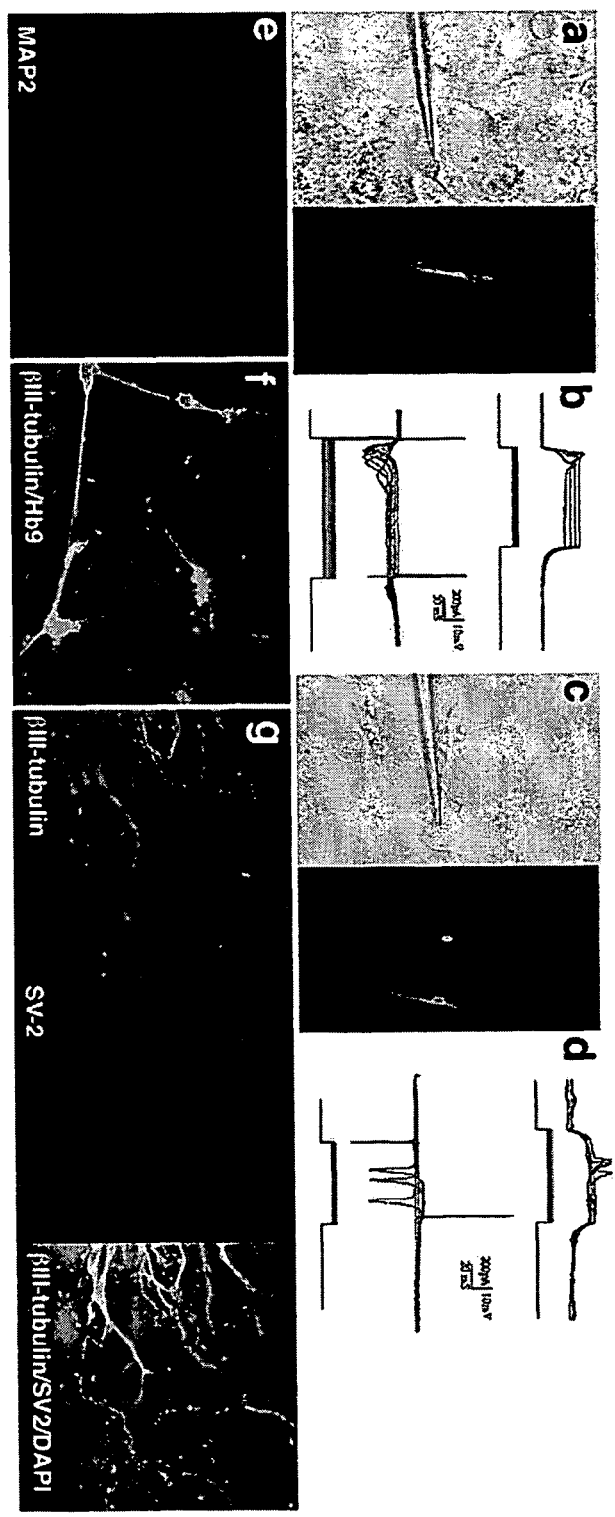
FIGURES 6A-G

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 1
cgaccatctg ccgctttg                                                 18

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 2
gccgcagctt acatgttct                                                19

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 3
ctaatctgaa tggtgctgtt tctatattg                                     29

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 4
ctctcttcct gcgcttttgc                                               20
```

US 8,263,406 B2

ENRICHED OR PURIFIED POPULATION OF MOTOR NEURONS AND ITS PREPARATION FROM A POPULATION OF EMBRYONIC STEM CELLS

This application claims the benefit of U.S. Provisional Patent Application Ser. No. 60/477,566, filed Jun. 11, 2003.

The present invention was made with funding from the National Institutes of Health Grant No. RO1NS33106. The United States Government may have certain rights.

FIELD OF THE INVENTION

The present invention is directed to an enriched or purified population of motor neurons and its isolation from a population of embryonic stem cells.

BACKGROUND OF THE INVENTION

Human ES (hES) cells have been shown to generate the entire range of major somatic cell lineages of the CNS (Reubinoff et al., "Embryonic Stem Cell Lines from Human Blastocysts: Somatic Differentiation In Vitro," *Nat Biotechnol* 18:399-404 (2000); Zhang et al., "In vitro Differentiation of Transplantable Neural Precursors from Human Embryonic Stem Cells," *Nat Biotechnol* 19:1129-1133 (2001); Schuldiner et al., "Induced Neuronal Differentiation of Human Embryonic Stem Cells," *Brain Res* 913:201-205 (2001); Carpenter et al., Characterization and Differentiation of Human Embryonic Stem Cells," *Cloning Stem Cells* 5:79-88 (2003); Park et al., "Generation of Dopaminergic Neurons In Vitro from Human Embryonic Stem Cells Treated with Neurotrophic Factors," *Neurosci Lett* 359:99-103 (2004)) and thus represent a potentially important source for cell-based therapies of CNS diseases. Most of the studies aimed at generating CNS specific phenotypes from hES cells have succeeded in partially directing these cells towards generation of neural stem cells (NSC), which have then been shown to give rise to a mixture of neural phenotypes. However, the selective production and isolation of specific clinically important neuronal and glial phenotypes from hES cells is yet to be accomplished. Indeed, to date no prospectively defined neuronal phenotype has yet been either induced or selected from hES cell cultures.

In contrast, a variety of specific neuronal phenotypes have been selectively induced in murine ES cell cultures using extracellular factors (Brustle et al., "Embryonic Stem Cell-derived Glial Precursors: A Source of Myelinating Transplants," *Science* 285:754-756 (1999); Kawasaki et al., "Induction of Midbrain Dopaminergic Neurons from ES Cells by Stromal Cell-derived Inducing Activity," *Neuron* 28:31-40 (2000); Lee et al., "Efficient Generation of Midbrain and Hindbrain Neurons from Mouse Embryonic Stem Cells," *Nat Biotechnol* 18:675-679 (2000); Liu et al., "Embryonic Stem Cells Differentiate into Oligodendrocytes and Myelinate in Culture and After Spinal Cord Transplantation," *Proc Natl Acad Sci USA* 97:6126-6131 (2000); Wichterle et al., "Directed Differentiation of Embryonic Stem Cells into Motor Neurons," *Cell* 110:385-397 (2002); Barberi et al., "Neural Subtype Specification of Fertilization and Nuclear Transfer Embryonic Stem Cells and Application in Parkinsonian Mice," *Nat Biotechnol* 21:1200-1207 (2003), or a combination of extracellular factors and genetic manipulation (Kim et al., "Dopamine Neurons Derived from Embryonic Stem Cells Function in an Animal Model of Parkinson's Disease," *Nature* 418:50-56 (2002); Billon et al., "Normal Timing of Oligodendrocyte Development from Genetically Engineered, Lineage-selectable Mouse ES Cells," *J Cell Sci* 115:3657-3665 (2002). In particular, both dopaminergic (Lee et al., "Efficient Generation of Midbrain and Hindbrain Neurons from Mouse Embryonic Stem Cells," *Nat Biotechnol* 18:675-679 (2000)) and cholinergic motor neurons (Wichterle et al., "Directed Differentiation of Embryonic Stem Cells into Motor Neurons," *Cell* 110:385-397 (2002)), expressing transcription factors typical of midbrain and spinal cord cells, respectively, have been selectively induced. In both cases, using key stage-specific factors well described in developmental mouse models (Durston et al., "Retinoic Acid Causes an Anteroposterior Transformation in the Developing Central Nervous System," *Nature* 340:140-144 (1989); Ericson et al., "Pax6 Controls Progenitor Cell Identity and Neuronal Fate in Response to Graded Shh Signaling," *Cell* 90:169-180 (1997); Ye et al., "FGF and Shh Signals Control Dopaminergic and Serotonergic Cell Fate in the Anterior Neural Plate," *Cell* 93:755-766 (1998); Muhr et al., "Assignment of Early Caudal Identity to Neural Plate Cells by a Signal from Caudal Paraxial Mesoderm," *Neuron* 19:487-502 (1999)), the two ventral neuronal phenotypes were generated: in the former case, dopaminergic neurons expressing transcription factors typical of the ventral mesencephalon were induced under the combined influence of sonic hedgehog (SHH) and FGF8, while in the latter, spinal cord motor neurons were generated by a combined treatment of SHH and RA. These studies show that signaling pathways delineated from various in vivo models of development can be used, to a certain limit, to selectively drive the induction and differentiation of defined neuronal phenotypes in mouse ES cells. However, specific isolation or purification of specific target cell types was not achieved in any of these studies. This is a particularly important issue in the use of hES-derived cells for cell-based therapy, since incompletely differentiated hES cells can be potentially tumorigenic upon implantation.

The present invention is directed to satisfying the need for a source of motor neurons from embryonic stem cells.

SUMMARY OF THE INVENTION

One aspect of the present invention is directed to a method of isolating an enriched or purified population of motor neurons from a population of embryonic stem cells. This method involves providing a population of embryonic stem cells and inducing production of motor neurons from the population of embryonic stem cells. A promoter or enhancer which functions only in motor neurons is selected, and a nucleic acid molecule encoding a marker protein under control of the promoter or enhancer is introduced into the induced population of embryonic stem cells. The motor neurons are allowed to express the marker protein and, the cells expressed in the marker protein are separated from the induced population of embryonic stem cells. As a result, an enriched or purified population of motor neurons is isolated.

Another embodiment of the present invention relates to a method of producing an enriched or purified population of motor neurons from a population of embryonic stem cells. According to this method, a promoter or enhancer which functions only in motor neurons is selected, and a nucleic acid molecule encoding a marker protein under control of the promoter or enhancer is introduced into a population of embryonic stem cells. The population of embryonic stem cells is induced to produce a mixed population of stem cells comprising motor neurons. The motor neurons are allowed to express the marker protein, and the cells expressing the marker protein are separated from the mixed population of cells. As a result, an enriched or purified population of motor neurons is isolated.

The present invention is also directed to an enriched or purified preparation of isolated motor neurons derived from human embryonic stem cells.

BRIEF DESCRIPTION OF THE DRAWINGS

FIGS. 1A-M show motor neurons (MN) induction from human ES cells. FIG. 1A is a schematic which outlines the induction of MNs from hES cells. FIGS. 1B-D show hES cells forming colonies on irradiated mouse embryonic fibroblast (MEF) cells, defined as undifferentiated by their expression of stage-specific embryonic antigen (SSEA-4) (FIG. 1C) and teratocarcinoma mucin-like antigen (TRA-1-81) (FIG. 1D). Over-confluent hES cells form rosettes (FIG. 1E) indicating density-induced neuralization, leading to largely neural embryoid bodies (EBs) (FIG. 1F). As shown in FIG. 1G, following RA and SHH treatment, EBs allowed to then differentiate in the presence of brain derived neurotrophic factor (BDNF)/glial-derived neurotrophic factor (GDNF)/ciliary neutrophic factor (CNTF), showed intense axonal outgrowth, often extending several millimeters. Immunolabeling revealed islet-1$^+$ (FIG. 1H)/βIII-tubulin$^+$ neurons (FIG. 1J) that co-localized with choline acetyl transferase (ChAT) (FIG. 1I) confirming motor neuron phenotype. As shown in FIGS. 1K-M, clusters of motor neurons, defined as both Hb9$^+$ (FIG. 1K) and βIII-tubulin$^+$ (FIG. 1l), were common in SHH and retinoic acid (RA) induced cultures.

FIGS. 2A-F show motor neuron induction from hES required the combined action of SHH and RA. FIGS. 2A-B show the percentage of βIII-tubulin-positive neurons (FIG. 2A) generated from the hES cells was not affected by the presence of RA or SHH, while there was a significant increase in the percentage of islet-1 (FIG. 2B) positive neurons in the combined presence of RA and SHH as compared to only RA. FIGS. 2C-D show similarly that there was a significant increase in the proportion on Hb9 (FIG. 2D) expressing βIII-tubulin-positive neurons (FIG. 2C) in the combined presence of RA and SHH. FIG. 2E has a graph on the left showing the proportion of βIII-tubulin-positive neurons in the total population and a graph on the right showing the percentage of βIII-tubulin-positive neurons that also expressed islet-1. FIG. 2F has a graph on the left showing the proportion of βIII-tubulin-positive neurons in the total population and graph on the right showing the percentage of βIII-tubulin-positive neurons that also expressed Hb9.

FIGS. 3A-G show motor neurons are specifically reported by a 3.6 kb enhancer within the Hb9 gene. As shown in FIG. 3A, the 3.6 kb Hb9 enhancer directed lacZ expression (FIG. 3A) to motor neurons, both spinal and cranial (nV and nVII), in E11.5 transgenic mice. As shown in FIG. 3B, the 3.6 kb Hb9 enhancer also directed motor neuron-specific expression of GFP in 10 wk human fetal spinal cord neurons as indicated by the co-localization of E/Hb9(3.6):GFP and Hb9 protein. As shown in FIGS. 3C-D, hES cells transfected with E/Hb9 (3.6):EGFP express GFP within 4 days of transfection of EBs generated in the presence of RA and SHH. FIG. 3E shows that E/Hb9(3.6):EGFP expression in cells derived from differentiated EBs was specific to motor neurons. This was confirmed by the co-localization of GFP with Hb9 protein. In FIGS. 3F-G, the MN phenotype of E/Hb9(3.6):EGFP$^+$ cells was also confirmed by the co-localization of green fluorescent protein (GFP) (FIG. 3F) with ChAT (FIG. 3G) and islet-1 (FIG. 3G).

FIGS. 4A-F show Hb9:GFP-based fluorescent activated cell sorting (FACS) highly enriches motor neurons from human ES cell culture. FIG. 4A is a FACS profile of human ES/EB-derived E/Hb9-3.6 kb:EGFP$^+$ cells, sorted 4 days after transfection. FIG. 4B shows that GFP+ cells were sorted onto neonatal rat skeletal myoblasts, to enhance their survival. It further shows a muscle substrate layer composed of almost 100% desmin+ cells. FIGS. 4C-F show FACS sorted E/Hb9:EGFP$^+$ (FIGS. 4C and E) cells expressed ChAT (FIGS. 4D and F). These cells were confirmed to express motor neuron-specific Hb9-protein (FIGS. 4D and F). All motor neurons showed in co-culture with skeletal myoblasts.

FIGS. 5A-B show MN induction followed by Hb9:GFP-based FACS enriched MNs and excluded undifferentiated cells. FIG. 5A is a graph showing the quantitative analysis of ES cell markers SSEA-4 and Tra-1-181 in conjunction with βIII-tubulin, Hb9 and islet-1 in naïve hES culture, differentiated unsorted cultures and differentiated sorted cells. FIG. 5B is a graphical representation of quantitative polymerase chain reaction (qPCR) analysis of Oct-4 a marker for pluripotent cells in conjunction with region specific transcription factors specifying midbrain (eng-1), interneuron (pax7) and MN (islet-1). No other transcripts other than islet-1 was present in the sorted population.

FIGS. 6A-G show HES-derived MNs achieved functional competence. E/Hb9-3.6 kb:EGFP$^+$ cells (insets in FIGS. 6A and 6C), subjected to whole cell patch clamp showed fast sodium-currents and action potentials (FIGS. 6B and D). FIG. 6E shows extension of axon bundles as long as 7 mm was a typical feature of E/Hb9-sorted human motor neurons. FIGS. 6F-G show Hb9$^+$ (FIG. 6F)/βIII-tubulin$^+$ motor neurons expressed synaptic vesicle protein-2 (FIG. 6G), indicating synaptic maturation.

DETAILED DESCRIPTION OF THE INVENTION

As used herein, the term "isolated" when used in conjunction with a nucleic acid molecule refers to: 1) a nucleic acid molecule which has been separated from an organism in a substantially purified form (i.e. substantially free of other substances originating from that organism), or 2) a nucleic acid molecule having the same nucleotide sequence but not necessarily separated from the organism (i.e. synthesized or recombinantly produced nucleic acid molecules).

The term "enriched" refers to a cell population that is at least 90% pure with respect to the index phenotype, regardless of its initial incidence in the population from which it was derived. The term "purified" refers to a cell population at least 99% pure with respect to the index phenotype, regardless of its initial incidence in the reference population.

One aspect of the present invention is directed to a method of isolating an enriched or purified population of motor neurons from a population of embryonic stem cells. This method involves providing a population of embryonic stem cells and inducing production of motor neurons from the population of embryonic stem cells. A promoter or enhancer which functions only in motor neurons is selected, and a nucleic acid molecule encoding a marker protein under control of the promoter or enhancer is introduced into the induced population of embryonic stem cells. The motor neurons are allowed to express the marker protein, and the cells expressed in the marker protein are separated from the induced population of embryonic stem cells. As a result, an enriched or purified population of motor neurons is isolated.

Preferably, these embryonic stem cells are of human origin. In carrying out the method of the present invention, those cells are kept in cell culture.

The present invention can be carried out using a promoter or enhancer that functions in and a nucleic acid encoding a marker protein, as described in U.S. Pat. No. 6,245,564 to Goldman et. al., which is hereby incorporated by reference in its entirety. In particular, this involves providing embryonic stem cells and selecting a promoter or enhancer which functions only in embryonic stem cells and not in other cell types. A nucleic acid molecule encoding a marker protein under control of the promoter or enhancer is introduced into the embryonic stem cells but not the other cell types, are allowed to express the marker protein. The cells expressing the marker protein are identified as being restricted to motor neurons and are separated from the mixed population to produce an isolated population of motor neurons.

Any promoter or enhancer which is specific for human white matter can be utilized in this process. "Specific", as used herein to describe a promoter or enhancer, means that the promoter or enhancer functions only in the chosen cell type. Suitable promoters or enhancers include Hb9 (Arber et al., "Requirement for the Homeobox Gene Hb9 in the Consolidation of Motor Neuron Identity," *Neuron* 23:659-674 (1999), which is hereby incorporated by reference in its entirety), choline acetyltransferase (Bausero et al., "Identification and Analysis of the Human Choline Acetyltransferase Gene Promoter," *Neuroreport* 4(3):287-90 (1993) and Lonnerberg et al., "Regulatory Region in Choline Acetyltransferase Gene Directs Developmental and Tissue-specific Expression in Transgenic Mice," *Proc Natl Acad Sci USA* 92(9):4046-50 (1995), which are hereby incorporated by reference in their entirety), Islet-1 (Ericson et al., "Early Stages of Motor Neuron Differentiation Revealed by Expression of Homeobox Gene Islet-1," *Science* 256:1555-1560 (1992), which is hereby incorporated by reference in its entirety), neurogenin-2 (Simmons et al., "Neurogenin2 Expression in Ventral and Dorsal Spinal Neural Tube Progenitor Cells is Regulated by Distinct Enhancers," *Dev Biol* 229(2):327-39 (2001) and Zhou et al., "The bHLH Transcription Factors OLIG2 and OLIG1 Couple Neuronal and Glial Subtype Specification," *Cell* 109(1):67-73 (2002), which are hereby incorporated by reference in their entirety), olig-2 (Takebayashi et al., "The Basic Helix-loop-helix Factor olig2 is Essential for the Development of Motoneuron and Oligodendrocyte Lineages," *Curr Biol* 12(13):1157-63 (2002), which is hereby incorporated by reference in its entirety), and erythropoietin receptor (Noguchi et al., "Cloning of the Human Erythropoietin Receptor Gene," *Blood* 78(10):2548-56 (1991); Liu et al., "Regulated Human Erythropoietin Receptor Expression in Mouse Brain," *J Biol Chem.* 272(51):32395-400 (1997); and Celik et al., "Erythropoietin Prevents Motor Neuron Apoptosis and Neurologic Disability in Experimental Spinal Cord Ischemic Injury," *Proc Natl Acad Sci USA* 9994):2258-63 (2002), which are hereby incorporated by reference in their entirety).

The marker protein is preferably a green fluorescent protein. The isolated nucleic acid molecule encoding a green fluorescent protein can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the GFP. In one embodiment, the GFP can be from *Aequorea victoria* (U.S. Pat. No. 5,491,084 to Chalfie et al., which are hereby incorporated in their entirety). A plasmid designated pGFP 10.1 has been deposited pursuant to, and in satisfaction of, the requirements of the Budapest Treaty on the International Recognition of the Deposit of Microorganisms for the Purposes of Patent Procedure, with the American Type Culture Collection (ATCC), 12301 Parklawn Drive, Rockville, Md. 20852 under ATCC Accession No. 75547 on Sep. 1, 1993. This plasmid is commercially available from the ATCC and comprises a cDNA which encodes a green fluorescent protein of Aequorea victoria as disclosed in U.S. Pat. No. 5,491,084 to Chalfie et al., which is hereby incorporated in its entirety. A mutated form of this GFP (a red-shifted mutant form) designated pRSGFP-C1 is commercially available from Clontech Laboratories, Inc. (Palo Alto, Calif.).

Mutated forms of GFP that emit more strongly than the native protein, as well as forms of GFP amenable to stable translation in higher vertebrates, are now available and can be used for the same purpose. Alternatively, the GFP can be in humanized form (GFPh) (Levy, J., et al., *Nature Biotechnol.* 14:610-614 (1996), which is hereby incorporated in its entirety). Any nucleic acid molecule encoding a fluorescent form of GFP can be used in accordance with the subject invention.

Other suitable marker proteins include lacZ/beta-galactosidase or alkaline phosphatase.

Standard techniques are then used to place the nucleic acid molecule encoding marker protein-encoding nucleic acid molecule under the control of the chosen cell specific promoter. Generally, this involves the use of restriction enzymes and ligation.

The resulting construct, which comprises the nucleic acid molecule encoding the marker protein under the control of the selected promoter or enhancer (themselves a nucleic acid molecule) (with other suitable regulatory elements if desired), is then introduced into a plurality of cells which are to be sorted. Techniques for introducing the nucleic acid molecules of the construct into the plurality of cells may involve the use of expression vectors which comprise the nucleic acid molecules. These expression vectors (such as plasmids and viruses) can then be used to introduce the nucleic acid molecules into the plurality of cells.

Various methods are known in the art for introducing nucleic acid molecules into host cells. These include: 1) microinjection, in which DNA is injected directly into the nucleus of cells through fine glass needles; 2) dextran incubation, in which DNA is incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell; 3) calcium phosphate coprecipitation, in which cells efficiently take in DNA in the form of a precipitate with calcium phosphate; 4) electroporation, in which cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA); 5) liposomal mediated transformation, in which DNA is incorporated into artificial lipid vesicles, liposomes, which fuse with the cell membrane, delivering their contents directly into the cytoplasm; 6) biolistic transformation, in which DNA is absorbed to the surface of gold particles and fired into cells under high pressure using a ballistic device; and 7) viral-mediated transformation, in which nucleic acid molecules are introduced into cells using viral vectors. Since viral growth depends on the ability to get the viral genome into cells, viruses have devised efficient methods for doing so. These viruses include retroviruses, lentivirus, adenovirus, herpesvirus, and adeno-associated virus.

As indicated, some of these methods of transforming a cell require the use of an intermediate plasmid vector. U.S. Pat. No. 4,237,224 to Cohen and Boyer, which is hereby incorporated in its entirety, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook et al., *Molecular Cloning: A Laboratory Manual*, 2d Edition, Cold Spring Harbor Laboratory Press, Cold Spring Harbor, N.Y. (1989), which is hereby incorporated in its entirety.

In accordance with one of the above-described methods, the nucleic acid molecule encoding the GFP is thus introduced into a plurality of cells. The promoter or enhancer which controls expression of the GFP, however, only functions in the cell of interest. Therefore, the GFP is only expressed in the cell of interest. Since GFP is a fluorescent protein, the cells of interest can, therefore, be identified from among the plurality of cells by the fluorescence of the GFP.

The inducing step typically involves administering an inducer like retinoic acid, sonic hedgehog, or an agonist thereof. Such administration can be carried out by direct administration in vitro.

Any suitable means of detecting the fluorescent cells can be used. The cells may be identified using epifluorescence optics, and can be physically picked up and brought together by Laser Tweezers (Cell Robotics Inc., Albuquerque, New M.). They can be separated in bulk through fluorescence activated cell sorting, a method that effectively separates the fluorescent cells from the non-fluorescent cells.

By carrying out the method of the present invention, a variety of motor neurons can be obtained, including spinal motor neurons, cranial motor neurons, and visceral motor neurons.

Once the enriched or purified population of motor neurons is isolated in accordance with the present invention, those neurons can be transplanted into a subject. This may be accomplished either by transuterine intra-embryonic or intra-fetal injection, either into the spinal cord, brain stem, or brain; or by post-natal injection directly into these same areas. Such transplantation is expected to be beneficial in treating subjects with motor neuron diseases, including spinal muscular atrophy, amytrophic leteral sclerosis, inflammatory myeloradiculitis, infectious myeloradiculitis (including, but not limited to polio and other enteroviruses, tetanus, rabies, and diphtheria), and spinal chord trauma (including spinal root avulsion syndromes).

Human ES-derived motor neurons may be transplanted either prenatally into fetuses, or postnatally into newborns, infants or children, as a treatment for pediatric spinal muscular atrophies.

Human ES-derived motor neurons may be transplanted either postnatally into infants, children or adults, as a treatment for inflammatory myeloradiculitis.

Human ES-derived motor neurons may be transplanted either postnatally into infants, children or adults, as a treatment for infectious myeloradiculitis, such as that caused by polio, other enteroviruses, cytomegalovirus, herpes simplex, rabies, HIV.

Human ES-derived motor neurons may be transplanted either postnatally into infants, children or adults, as a treatment for spinal cord root avulsion, cauda equinae syndrome, or other forms of spinal cord injury, including both cervical and lumbar compressive myeloradiculopathies.

Another embodiment of the present invention relates to a method of producing an enriched or purified population of motor neurons from a population of embryonic stem cells. According to this method, a promoter or enhancer which functions only in motor neurons is selected, and a nucleic acid molecule encoding a marker protein under control of the promoter or enhancer is introduced into a population of embryonic stem cells. The population of embryonic stem cells is induced to produce a mixed population of stem cells comprising motor neurons. The motor neurons are allowed to express the marker protein, and the cells expressing the marker protein are separated from the mixed population of cells. As a result, an enriched or purified population of motor neurons is isolated.

In carrying out this aspect of the present invention, substantially the same reagents and steps described above are utilized.

The present invention is also directed to an enriched or purified preparation of hES cells stably transduced to incorporate E/Hb9:GFP, within which motor neurons might be readily recognized and extracted as they appear. In one embodiment, as described above, motor neurons may be extracted via FACS based upon GFP expressed under the control of the hb9 enhancer. In another embodiment, motor neurons may be extracted from hES pools using antibiotic selection, based on an Hb9-driven antibiotic resistance unit such as neo or puro. These may also be placed downstream to GFP under IRES control to permit either FACS or antibiotic-based selection.

Another aspect of the present invention relates to an enriched or purified preparation of isolated motor neurons derived from human embryonic stem cells. This preparation is formulated from the motor neurons described above.

The E/Hb9:GFP-transduced hES cells, stably transduced with this motor neuron reporter, might serve as screening vehicles for motor neuron inductive and supportive agents.

EXAMPLES

Example 1

Source of hES

The hES cells were derived from the H1 line (Thomson et al., "Embryonic Stem Cell Lines Derived from Human Blastocysts," *Science* 282:1145-1147 (1998), which is hereby incorporated by reference in its entirety). They were obtained from WiCell Research Institute, University of Wisconsin-Madison.

Example 2

Culturing and Passaging of hES Cells

Cells were maintained and passaged in co-cultures with mouse embryonic feeder cells (MEF) as per published protocols (Thomson et al 1998, which is hereby incorporated by reference in its entirety). Cultures are passaged every 7-14 days. To passage, hES cells were treated with collagenase type IV (200 units/ml) for 10 mins and scraped off the culture dish. The scraped cells were split 1:3-1:4 on MEF cultures in 6 well plates. The hES cells were fed every 24 hrs with KO-DMEM supplemented with 20% KO-Serum replacement (KO-medium) and bFGF (4 ng/ml) (Gibco). MEF cells for co-culture were established as follows: fibroblast cells, obtained from E14 mouse embryos, were grown to confluency in gelatin (0.1% W/V) coated flasks in DMEM supplemented with 10% fetal bovine serum (FBS). The cells were collected by trypsinization and irradiated at 4000 rads. The irradiated cells (185,000 cells per well) were re-plated on gelatin coated 6 well plates.

Example 3

Specification and Differentiation of Motor Neuron

A modified version of the protocol described in Wichterle et al., "Directed Differentiation of Embryonic Stem Cells into Motor Neurons," Cell 110:385-397 (2002), which is hereby incorporated by reference in its entirety, was used for induction and differentiation of motor neurons from hES cells (FIG. 1A). For caudalization and specification to motor neurons, 90% confluent hES cell cultures were dissociated to form embryoid bodies (EB) in suspension dishes (Ultra low cluster 6 well plates, Corning) in KO-medium containing 10 µM all-trans retinoic acid and 100 nM of a modified version of the active N-terminal peptide of human sonic hedgehog (Curis, Mass.). Fresh RA was added every day and fresh medium along with SHH replaced every 72 hrs. After 6-8 days, differentiation of motor neurons was induced by plating the spheres formed onto poly-ornithin/fibronectin coated plates in DMEM/F12 supplemented with N2 (Gibco), GDNF (20 ng/ml), BDNF (20 ng/ml), or neurotrophin 4 (NT4) (20 ng/ml), CNTF (20 ng/ml), B27 (1X) and 2% FBS. After 7-14 days, cultures were either fixed for immunocytochemistry or used for physiology.

Example 4

Construction of 3.6 kb Hb9 Enhancer:EGFP

First the hsp68-EGFP cassette from Asshsp68-EGFP was cloned into the SpeI restriction site of pBluescript. The 3.6 kb Hb9-hsp68-EGFP was then generated by inserting the XhoI-SseI fragment of 3.6 kb Hb9 enhancer from the 9 kb Hb9 promoter upstream of hsp68 promoter by using XhoI and PstI sites.

Example 5

Transfection of hES Culture with E/Hb9:EGFP hES cultures that were 80-90%% confluent were dissociated with collagenase and cocultured with MEF at a 70% confluency. After 24 hrs, the cells were transfected with the 3.6 kb Hb9 enhancer:EGFP plasmid in Opti-MEM (Gibco) using the Fugene transfection reagent (Roche) for 8 hrs. The transfection was terminated by adding equal volume of KO-medium overnight. The transfected hES cells were then induced to form EBs as described in the earlier section. Expression of EGFP was usually seen within 3-5 days after EB induction.

Example 6

Flow Cytometry and Sorting

The EBs were first treated with a mixture of Trypsin/EDTA and Dnase-I (Sigma) for 5 minutes. The enzymatic reaction was stopped with 10% FBS, and the cells were dissociated by mechanical trituration through a fire polished glass pipette. The cells were collected by centrifugation at 1200 rpm for 5 minutes and re-suspended in phenol red free DMEM/F12. The cells were filtered through a 40 um mesh and sorted for EGFP-expressing cells on a FACS Vantage SE (Becton-Dickinson). Untransfected cells were used as a control to set the cutoff value for background fluorescence. Positive cells were either directly collected on rat skeletal muscle cell cultures (described supra) or collected and frozen immediately for RNA extraction for qPCR.

Example 7

Coculturing of Sorted Cells with Skeletal Muscle Cells

Skeletal muscle cell cultures were established from postnatal day 1 rats. Thigh muscle was collected, chopped into small pieces and dissociated by treating sequentially for 30 mins each with collagenase type III/collagenase type IV (200 U/ml, Gibco) followed by trypsin/EDTA and DnaseI. The enzyme reaction was stopped by treating with 10% FBS, and the cells were mechanically dissociated by trituration through a fire polished glass pipette, collected by spinning for 5 mins at 12000 rpm. The cells were resuspended in high glucose DMEM supplemented with 10% FBS and 10% horse serum and 100,000 cells plated on 0.5% gelatin coated 35 mm tissue culture plates. After 7 days in vitro, the percentage of muscle cells, as determined by expression of desmin, was >70%. Sorted E/Hb9:EGFP positive motor neurons were co-cultured on 10 day old muscle cell cultures.

Example 8

Immunocytochemistry

Cells were stained at different stages of culture for the following: Tra 1-81 (Mouse IgG, 1:200), SSEA-4 (supernatant, mouse IgG, 1:50, DSHB), βIII-tubulin (mouse IgG; 1:400, Covance), Islet1 (supernatant, mouse IgG, 1:50, Developmental Studies Hybridoma Bank from the University of Iowa (DSHB)), Hb9 (supernatant, mouse IgG, 1:50, DSH), ChAT (Rabbit IgG, 1:200, Chemicon), desmin (Rabbit IgG, 1:200, Sigma), and GFP (mouse IgG, 1:100). Cells were fixed with 4% paraformaldehyde for 5 minutes and incubated with primary antibody for 24 hrs at 4° C. and fluorescent or biotin labeled secondary antibodies for 2 hrs at room RT. For staining with DAB (Sigma), the ABC kit (vector) was used.

Example 9

Quantitative PCR (qPCR)

Samples in triplicates (25 ng total RNA) each for reverse transcription (RT)+ samples and RT− control were prepared. These were first subjected to reverse transcription using Taqman RT kit (Applied Biosystems). qPCR reactions were done by using either SYBR Green PCR Master Mix or TaqMan universal PCR Master Mix (both from Applied Biosystems). Of the RT products, 1/50 the total amount was used for each qPCR reaction. Primers for En1 (Assay ID Hs00154977_m1) and Pax7 (Assay ID Hs00242962_m1) were ordered from assays-on-demand from Applied Biosystems. Primers for Oct3/4 and islet-1 were as follows: Oct3/4, Forward: cgaccatctgccgctttg (SEQ ID NO: 1), Reverse: gccgcagcttacatgttct (SEQ ID NO: 2) and islet-1, Forward: CTAATCTGAATG- GTGCTGTTTCTATATTG (SEQ ID NO: 3), Reverse: CTCTCTTCCTGCGCTTTTGC (SEQ ID NO: 4). The average value of multiple RT+ samples was normalized by using VIC 18S primers and TaqMan probe as an internal control. The values were expressed as fold increase or decrease compared to naïve hES cells.

Example 10

Calcium Imaging

After 2 weeks of induction of motor neuron differentiation, the E/Hb9:EGFP expressing cultures were challenged with depolarizing stimuli of either 100 μM glutamate or 60 mM $K^+$, during which their cytosolic calcium levels were observed. Calcium imaging was performed using confocal microscopy of cultures loaded with fluo-3 acetoxymethylester (fluo-3, Molecular Probes, Oreg.), as previously described (Roy et al., "In vitro Neurogenesis by Progenitor Cells Isolated from the Adult Human Hippocampus," Nat Med 6:271-277 (2000) and Nunes et al., "Identification and Isolation of Multipotential Neural Progenitor Cells from the Subcortical White Matter of the Adult Human Brain," Nat Med 9(4):439-47 (2003), which are hereby incorporated by reference in their entirety).

Example 11

Electrophysiology

Sister cultures to those subjected to calcium imaging were also assessed by whole-cell patch clamp analysis. Whole-cell voltage-clamped recordings of E/Hb9:EGFP expressing cells were performed as previously described (Roy et al., "In vitro Neurogenesis by Progenitor Cells Isolated from the Adult Human Hippocampus," Nat Med 6:271-277 (2000), which is hereby incorporated by reference in its entirety) under differential inference contrast (DIC) optics at 23-24° C. A holding potential of −60 mV and voltage steps of 10 mV with 100 ms durations were applied to the recorded cells through the patch electrodes. Recordings were carried out using Axopatch 200B and PCLAMP 7.0. Signals were sampled every 50 μs, and all analysis and processing were performed as described.

Example 12

Induction of Motor Neurons from hES Cells was RA and SHH Dependent

To determine if hES cells had the capacity to respond to the caudalizing effects of RA and the ventralizing effects of SHH to generate MNs (Wichterle et al., "Directed Differentiation of Embryonic Stem Cells into Motor Neurons," Cell 110:385-397 (2002), which is hereby incorporated by reference in its entirety), hES cells were raised to 90% confluency before inducing them to form EBs in suspension cultures. EBs were raised in the presence of RA (10 uM) alone or RA with SHH (FIGS. 1A-E). EBs raised in the absence of both RA and SHH were included as controls. After 8-9 days in suspension, the EBs were induced to differentiate in the presence of FBS/B27 and neurotrophic factors BDNF/GDNF/CNTF, that have been shown to additively and synergistically increase motor neuron differentiation, survival, and neurite length extension (Zurn et al., "Combined Effects of GDNF, BDNF, and CNTF on Motoneuron Differentiation In vitro," J Neurosci Res 44:133-141 (1996), which is hereby incorporated by reference in its entirety). After a week in a differentiated condition, the cells were fixed and the percentage of βIII-tubulin expressing neurons was determined. Among the total βIII-tubulin expressing neurons, the percentage of motor neurons was quantified by either staining for the transcription factor islet-1, a member of the LIM/homeobox gene family expressed by motor neurons (Ericson et al., "Early Stages of Motor Neuron Differentiation Revealed by Expression of Homeobox Gene Islet-1," Science 256:1555-1560 (1992), which is hereby incorporated by reference in its entirety) or for HB9 (FIGS. 1F-I). Motor neuron identity was further confirmed by staining for the neurotransmitter choline acetyltransferase (ChAT).

The presence of RA or SHH or both had no effect on the proportion of neurons generated from the differentiated EBs. The percentage of neurons generated in all the three conditions, −RA/SHH−, RA+/SHH− and RA+/SHH+ was, on an average, around 30% (FIGS. 2E and 2F). The proportion of neurons expressing the motor neuron phenotype, however, was increased by >4 fold in the combined presence of RA and Shh: 56.07±9.95% of the βIII-tubulin expressing neurons expressed islet-1/ChAT (FIG. 2E) and 37.43±3.34% expressed Hb9 (FIG. 2F). In −RA/SHH− and RA+/SHH− conditions, the population of islet-1/ChAT expressing neurons ranged from 3%-10% and of Hb9 expressing neurons raged from 3%-6% (FIGS. 2E and 2F). Since the effect of SHH is very concentration dependent (Ericson et al., "Two Critical Periods of Sonic Hedgehog Signaling Required for the Specification of Motor Neuron Identity," Cell 87:661-673 (1996); Briscoe et al., "The Specification of Neuronal Identity by Graded Sonic Hedgehog Signalling," Semin Cell Dev Biol 10:353-362 (1999), which are hereby incorporated by reference in their entirety) the effect of SHH concentration, ranging from 50-500 nM, on MN generation, was also quantified. The proportion of motor neurons generated maximized at 200 nM SHH and remained similar at concentrations 300 nM and 500 nM. Therefore, all the studies reported were done at 200 nM of SHH.

Example 13

Motor Neurons May be Identified on the Basis of Hb9-Driven GFP

To isolate motor neurons generated within the RA/SHH-induced neuronal pool, a selection cassette was established based on the promoter for the motor neuron specific transcription factor Hb9 (Arber et al., "Requirement for the Homeobox Gene Hb9 in the Consolidation of Motor Neuron Identity," Neuron 23:659-674 (1999), which is hereby incorporated by reference in its entirety). The 9 kb 5' regulatory region for the Hb9 gene contains the information sufficient to direct expression to somatic motor neurons in transgenic mice (Wichterle et al., "Directed Differentiation of Embryonic Stem Cells into Motor Neurons," Cell 110:385-397 (2002), which is hereby incorporated by reference in its entirety). In order to establish selection constructs small enough for somatic transfection, homology screening was used to identify a 3.6 kb upstream enhancer. This enhancer, linked with β-globin gene as a basal promoter, proved selective for motor neurons in both transgenic mice and transfected dissociates of the human fetal spinal cord (FIGS. 3A-C). This fragment was then placed 5' to the stronger heat shock protein-68 basal promoter, and the resulting construct was then ligated to EGFP to establish the E/Hb9-3.6 kb:EGFP selection vector. When hES cells were transfected with pE/Hb9-3.6 kb:EGFP and immediately induced to form embryoid bodies (EBs) in the presence of RA and SHH, GFP expression was observed within 5 days after transfection (FIG. 4A). After 9 days in the presence of RA and SHH, the embryoid bodies were induced to differentiate on poly-omithine/fibronectin coated dishes in the presence of FBS/B27BDNF/GDNF/CNTF. After 5 days of differentiation, GFP expressing cells, with a distinct neuronal morphology, could be seen migrating out of the EBs (FIG. 3D). It was found that this construct reliably and specifically recognized MNs as confirmed by the co-localization of the GFP expressing cells Hb9, islet-1 and ChAT (FIGS. 3E-3G).

Example 14

Hb9:GFP-based FACs May be Used to Select hES-Generated Motor Neurons

For isolation of the generated MN pool, the E/Hb9-3.6 kb:EGFP-expressing cells were sorted at the EB stage. Flow cytometry analysis showed the EGFP expressing cells constitute $1.09\pm0.26\%$ (n=3, average±SE) of the total population (FIG. 4A). However, if the average transfection efficiency of 17%, which was determined by transfecting parallel cultures of hES cells with a EGFP construct driven by the nonspecific CMV promoter, is considered, MNs represent 6.4% of the total sorted population. The FACS sorted cells were plated in differentiation medium consisting of p-omithine/fibronectin substrate and DMEM/F12 supplemented with FBS/B27/BDNF/GDNF/CNTF. While efficient survival and differentiation of the generated MNs in unsorted mixed populations under similar conditions was achieved, the FACS-purified cells were unable to survive beyond a few days, let alone achieve differentiation. In the mixed milieu of the unsorted population, the generated MNs would be subjected to various types of neurotrophic and contact mediated support, combinations considered to be important for the survival of MN (Sendtner et al., Developmental Motoneuron Cell Death and Neurotrophic Factors," *Cell Tissue Res* 301:71-84 (2002), which is hereby incorporated by reference in its entirety), and demonstrate good MN survival and differentiation. Therefore, it was decided to co-culture the FACS sorted MNs with skeletal muscle cells derived from neonatal rats (FIG. 4B). In this coculture system, 100% of the FACS sorted MN survived and were able to achieve differentiation as indicated by the expression of Hb9, βIII-tubulin and ChAT (FIGS. 4C-4F).

Example 15

Sequential Induction and Hb9-based FACS Removed Undifferentiated ES Cells While Enriching the MN Pool It was next desired to determine if all naïve/undifferentiated hES cells were eliminated by the combination of RA/Shh exposure and pE/Hb9-3.6 kb:EGFP based FACS sorting. For this, cultures were quantified immunocytologically for ES cell specific markers, SSEA-4 and Tra-1-81 at the following three stages; (a) ES cells, (b) Mixed unsorted RA/SHH induced and differentiated cultures and (c) FACS sorted E/Hb9-3.6 kb:EGFP-expressing cells differentiated in co-cultures with skeletal muscle cells. At the ES cell stage (a), $75.23\pm4.65\%$ and $68.27\pm5.80\%$ of the cells expressed SSEA-4 and Tra-1-81, respectively (FIG. 5A). In unsorted differentiated cultures (b), the proportion of cells expressing SSEA-4 and Tra-1-81 had fallen down to $1.33\pm0.95\%$ and $0.60\pm0.39\%$, respectively, while no SSEA-4 and Tra-1-81 positive cells were seen in the sorted cultures (c). It was also quantified, at all the three stages, the proportion of MNs in parallel cultures. Some spontaneous neuronal differentiation, as indicated by the presence of $0.63\pm0.43\%$ and $0.27\pm33\%$ cells expressing Hb9/βIII-tubulin and Islet/ChAt, respectively, was observed in hES cultures. In FACS sorted cultures, almost $90.1\pm2.0\%$ of the cells expressed Hb9/βIII-tubulin and $88.63\pm1.96\%$ expressed islet1/ChAT (FIG. 5A).

The presence/absence of naïve/undifferentiated hES cells and the purity of the sorted MNs was also confirmed by quantitative PCR (qPCR). For this, mRNA was extracted from the sorted cells immediately post-sort and mRNA from three sets of experiments was pooled together. Applicants then assayed for oct-4, a transcription factor important in maintaining totipotency in ES cells (Pesce et al., "Oct-4: Lessons of Totipotency from Embryonic Stem Cells," *Cells Tissues Organs* 165:144-152 (1999), which is hereby incorporated by reference in its entirety). To confirm for the purity of the sorted population, it was assayed for positional-specific transcription factors, engrailed-1 (Eng-1) which is ventral midbrain specific (Shamim et al., "Sequential Roles for Fgf4, En1 and Fgf8 in Specification and Regionalisation of the Midbrainm" *Development* 126:945-959 (1999) and Smidt et al., "Molecular Mechanisms Underlying Midbrain Dopamine Neuron Development and Function," *Eur J Pharmacol* 480:75-88 (2003), which are hereby incorporated by reference in their entirety) and Pax 7, which is specific to the dorsal and intermediate spinal cord (Lee et al., "The Specification of Dorsal Cell Fates in the Vertebrate Central Nervous System," *Annu Rev Neurosci* 22:261-294 (1999), which is hereby incorporated by reference in its entirety). The base line level for each of the transcripts was set at 100% for hES cells and the values for the sorted and unsorted cells was quantified relative to the 100% base line. With differentiation, the level of oct-4 mRNA fell to 1.6% and was almost undetectable in FACS sorted cells. Similarly Eng-1, which was increased to 211.18% in the mixed unsorted pool, was no longer present in the sorted pool. Pax7, which decreased to 11.43% in the unsorted pool, was undetectable in the sorted cells. mRNA for islet-1, which was included as a marker for MN, was present at 573% which was 14-fold more than what was present in the unsorted pool.

Example 16

Human ES-derived Motor Neurons Achieved Physiological Functional Maturation and Extended Neuritis Spanning Long Distances It was next asked whether hES-derived motor neurons developed the fast sodium currents and action potentials characteristic of electrophysiologically-competent neurons. For this purpose, whole-cell patch clamp recording during current stimulation was used to assess the response characteristics of hES-derived motor neurons cultures allowed to differentiate for two weeks. A total of 25 hES-derived E/Hb93.6 kb:EGFP+ motor neurons were patched and recorded. Action potentials were noted after positive current injection of >800 pA. Of these, 6 showed action potential >400 pA, (588±89) (FIGS. 6A-6D) compatible with the fast sodium currents observed in neuronal depolarization. This is of import, because sodium currents constitute the ionic mechanism underlying the neuronal action potential.

It was then asked whether hES-derived motor neurons would be competent enough to extend axons through long distances to establish contacts with target cell. For this, SHH/RA induced hES cells were permitted to differentiate for 4 weeks. A consistent observation in these long-term differentiated cultures was the presence of thick fascicle-like groups of axons migrating long distances (FIGS. 6E and 6F) and this cluster exclusively belonged to Hb9 positive neurons. Such a group of axons average 5.35 mm in length. Non-Hb9 positive neuronal clusters almost never showed this feature. The axonal-cluster also exhibited vesicle formation at their axon terminals (FIG. 6G). Immunocytochemistry for synaptic vesicle associated protein 2 (SV2) showed strong colocalization along the axonal terminals, indicating synaptic maturation of the hES-derived MNs.

The selective induction and isolation of somatic motor neurons from human embryonic stem cells is reported here. It has been found that SHH/RA-based motor neuron induction, previously reported as effective in driving motor neuron differentiation in murine ES cells (Wichterle et al., "Directed Differentiation of Embryonic Stem Cells into Motor Neurons," Cell 110:385-397 (2002), which is hereby incorporated by reference in its entirety), was similarly effective in generating motor neurons from neuralized human ES cells. In addition, the issue of isolating motor neurons from a mixed ES culture by using fluorescence-activated cell sorting, based on Hb9 promoter-driven GFP, has been addressed. This approach allowed isolation of ES cell-derived human motor neurons to apparent purity. This was done while concurrently depleting the sorted population of undifferentiated ES cells, as reflected in an absolute depletion of oct1/oct4/SSEA+ cells from the sorted pool. The sorted human motor neurons expressed an antigenic factor profile typical of somatic motor neurons, Isl1+/Hb9+/ChAT+. Taken together, their expression of choline acetyl-transferase, and fast sodium currents on whole cell patch clamp analysis, strongly suggest that these cells may serve as functional cholinergic neurons.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An in vitro method of isolating an enriched or purified population of human motor neurons from a population of human embryonic stem cells comprising:
   providing a population of human embryonic stem cells;
   culturing the population of human embryonic stem cells under conditions effective to promote neuralization and embryoid body formation;
   administering retinoic acid and sonic hedgehog to the cultured population of human embryoid bodies in an amount effective to induce the production of motor neurons from the population of human embryoid bodies;
   introducing a nucleic acid molecule encoding a marker protein operably linked to a heterologous basal promoter and a mouse 3.6 kb XhaI-SseI Hb9 enhancer region into the population of human embryoid bodies which have been subjected to said administering, wherein the enhancer region selectively directs expression of the marker protein to human motor neurons, is isolated from the 9 kb Hb9 promoter region, and is placed upstream of said heterologous basal promoter;
   allowing the motor neurons to express the marker protein; and
   separating the cells expressing the marker protein from the population of human embryoid bodies which have been subjected to said inducing, whereby an enriched or purified population of human motor neurons is isolated.

2. The method of claim 1, wherein said introducing comprises viral mediated transduction of the population of human embryonic stem cells which have been subjected to said inducing.

3. The method of claim 2, wherein said viral mediated transduction comprises adenovirus-mediated transduction, retrovirus-mediated transduction, lentivirus-mediated transduction, or adeno-associated virus-mediated transduction.

4. The method of claim 1, wherein said introducing comprises electroporation.

5. The method of claim 1, wherein said introducing comprises biolistic transformation.

6. The method of claim 1, wherein said introducing comprises liposomal mediated transformation.

7. The method of claim 1, wherein the marker protein is a fluorescent protein and said separating comprises fluorescence activated cell sorting.

8. The method of claim 1, wherein the marker protein is either lacZ/beta-galactosidase or alkaline phosphatase.

9. The method of claim 1, wherein the motor neurons are spinal motor neurons, cranial motor neurons, or visceral motor neurons.

10. An in vitro method of producing an enriched or purified population of human motor neurons from a population of human embryonic stem cells comprising:
    culturing the population of human embryonic stem cells under conditions effective to promote neuralization and embryoid body formation;
    introducing a nucleic acid molecule encoding a marker protein operably linked to a heterologous basal promoter and a mouse 3.6 kb XhaI-SseI enhancer region of the Hb9 gene promoter into the cultured population of human embryoid bodies, wherein the enhancer region selectively directs expression of the marker protein to human motor neurons, is isolated from the 9 kb Hb9 promoter region, and is placed upstream of said heterologous basal promoter;
    administering retinoic acid and sonic hedgehog to the population of human embryoid bodies, subjected to said introducing, in an amount effective to induce the production of a mixed population of human cells comprising motor neurons;
    allowing the motor neurons to express the marker protein; and
    separating the cells expressing the marker protein from the mixed population of human cells, whereby an enriched or purified population of human motor neurons are isolated.

11. The method of claim 10, wherein said introducing comprises viral mediated transduction of the population of human embryonic stem cells.

12. The method of claim 11, wherein said viral mediated transduction comprises adenovirus-mediated transduction, retrovirus-mediated transduction, lentivirus-mediated transduction, or adeno-associated virus-mediated transduction.

13. The method of claim 10, wherein said introducing comprises electroporation.

14. The method of claim 10, wherein said introducing comprises biolistic transformation.

15. The method of claim 10, wherein said introducing comprises liposomal mediated transformation.

16. The method of claim 10, wherein the marker protein is a fluorescent protein and said separating comprises fluorescence activated cell sorting.

17. The method of claim 10, wherein the marker protein is either lacZ/galactosidase or alkaline phosphatase.

18. The method of claim 10, wherein motor neurons are spinal motor neurons, cranial motor neurons, or visceral motor neurons.

* * * * *